United States Patent
Yaros et al.

(10) Patent No.: US 11,504,050 B1
(45) Date of Patent: Nov. 22, 2022

(54) REHABILITATION DEVICE FOR THE VESTIBULAR OCULAR SYSTEM AND OTHER NEUROCOGNITIVE FUNCTIONS

(71) Applicants: Ethan Yaros, East Brunswick, NJ (US); Mark Yaros, East Brunswick, NJ (US)

(72) Inventors: Ethan Yaros, East Brunswick, NJ (US); Mark Yaros, East Brunswick, NJ (US)

( * ) Notice: Subject to any disclaimer, the term of this patent is extended or adjusted under 35 U.S.C. 154(b) by 365 days.

(21) Appl. No.: 16/879,900

(22) Filed: May 21, 2020

Related U.S. Application Data

(60) Provisional application No. 62/851,408, filed on May 22, 2019.

(51) Int. Cl.
| | |
|---|---|
| *A61B 5/00* | (2006.01) |
| *G01B 3/04* | (2006.01) |
| *A61B 5/16* | (2006.01) |
| *A61H 5/00* | (2006.01) |

(52) U.S. Cl.
CPC .......... *A61B 5/4023* (2013.01); *A61B 5/163* (2017.08); *A61B 5/743* (2013.01); *A61H 5/005* (2013.01); *G01B 3/04* (2013.01)

(58) Field of Classification Search
CPC ....... A61B 5/4023; A61B 5/163; A61B 5/743; A61H 5/005; G01B 3/04
See application file for complete search history.

(56) References Cited

U.S. PATENT DOCUMENTS

| | | | |
|---|---|---|---|
| 5,838,420 A | 11/1998 | MacGregor Donaldson | |
| 5,942,954 A | 8/1999 | Galiana et al. | |
| 5,984,475 A | 11/1999 | Galiana et al. | |
| 6,036,046 A | 5/2000 | Allum | |
| 9,072,481 B2 | 7/2015 | Shelhamer | |
| 9,167,998 B2 | 10/2015 | Crane | |
| 9,370,302 B2 | 6/2016 | Krueger | |

(Continued)

OTHER PUBLICATIONS

"StableEyes—A Portable Vestibular Rehabilitation Device" found at https://ieeexplore.ieee.org/document/8357602 discloses vestibulo-ocular reflex training systems. Related Youtube video.

*Primary Examiner* — Collin X Beatty
(74) *Attorney, Agent, or Firm* — John Rizvi; John Rizvi. P.A.—The Patent Professor ®

(57) ABSTRACT

A medical rehabilitation device for clinically rehabilitating individuals suffering from medical conditions affecting the vestibular ocular system, and other neurocognitive functions. The rehabilitation device includes a support base having an elongate slot, and a plurality of arms adjustably attached to the support base via the elongated slot, where each arm includes a magnetic strip for selectively positioning visual targets thereon to solicit patient recognition of colors and positions of the visual targets during both vestibular ocular reflex, and other neurocognitive exercises. Each arm and the support base includes measurement markings extending along the top longitudinal surface of each arm adjacent the magnetic strips and along the elongate slot, respectively, to provide measured and objective charted indicators for vestibular ocular reflex and other neurocognitive functions over time. The arms are adjustable in horizontal, vertical, and diagonal positions to selectively adjust the difficulty of the exercises in a plane of vision.

20 Claims, 5 Drawing Sheets

(56) References Cited

U.S. PATENT DOCUMENTS

| | | |
|---|---|---|
| 9,610,029 B2 | 4/2017 | Alberts |
| 9,814,430 B1 | 11/2017 | Berme et al. |
| 10,010,248 B1 | 7/2018 | Shearer |
| 2009/0021698 A1* | 1/2009 | Bardenstein ............. A61B 3/10 |
| | | 351/245 |
| 2009/0240172 A1 | 9/2009 | Fernandez Tournier et al. |
| 2011/0184498 A1 | 7/2011 | Donley |
| 2016/0213248 A1 | 7/2016 | Budagher |
| 2018/0008141 A1 | 1/2018 | Krueger |
| 2018/0090020 A1 | 3/2018 | Mango et al. |
| 2018/0296089 A1 | 10/2018 | Carson et al. |

* cited by examiner

REHABILITATION DEVICE FOR THE VESTIBULAR OCULAR SYSTEM AND OTHER NEUROCOGNITIVE FUNCTIONS

CROSS-REFERENCE TO RELATED APPLICATIONS

This application claims the benefit of U.S. Provisional Patent Application Ser. No. 62/851,408, filed on May 22, 2019, which is incorporated by reference herein in its entirety.

FIELD OF THE INVENTION

The present invention relates to medical rehabilitation devices, and more particularly, to a rehabilitation device used for clinically rehabilitating individuals suffering from medical conditions affecting the vestibular ocular system, and other neurocognitive functions.

BACKGROUND OF THE INVENTION

Rehabilitation devices, methods and techniques have proven beneficial for individuals who suffer from a variety of medical conditions that affect both mental and physical attributes of the person. Rehabilitation centers, clinics, and departments of hospitals generally have skilled workers and necessary equipment needed to rehabilitate individuals and improve upon deficiencies, disorders, or other impairments affecting speech, dexterity, mobility, neurocognitive conditions, auditory, nerves, muscles, and bones of the individuals as a result of illness, injury, degeneration, or age. For example, it is common for individuals who have sustained injuries as a result of an accident, surgery, or a fall to undergo a series of therapy sessions in an effort to strengthen and improve the functional use of a person's physical capacities. Physical therapists, occupational therapists, and athletic trainers are trained to employ particular techniques and equipment designed to rehabilitate various medical impairments of individuals of all ages, young and old alike. Designated skill sets used for rehabilitation are specifically tailored for the particular types of impairment involved. As such, it is very common to visit rehabilitation centers or clinics and see trained workers using a variety of different tools and equipment while individuals undergo exercise therapies.

Rehabilitation is often prescribed to individuals who also suffer from medical conditions affecting the vestibular ocular system as well. The human vestibular system generally includes various parts of the inner ear such as arteries, saccule, utricle, and semicircular canals that are linked to the brain to effectively control and coordinate a person's balance and eye movements. The inner ear and brain work together to keep a person's eyes stable and focused on objects as the person moves around. Functional attributes of the vestibular ocular system are often affected by a host of conditions caused by aging, injury such as a concussion, degeneration, Meniere's disease, and infections such as labyrinthitas-ear infection, and vestibular neuritis-a viral infection. Vestibular ocular dysfunction is often associated with certain symptoms including imbalance, spatial disorientation, cognitive impairments, and hearing deficiencies, to name a few. One common symptom that is often experienced by individuals is benign paroxysmal positional vertigo (BPPV) and dizziness. Vertigo is a condition in which individuals feel dizzy and have difficulty retaining balance when walking, sitting, or transitioning between sitting and standing. More severe cases of vertigo often involve individuals feeling nauseous, extremely light headed, have difficulty coordinating movements, and having visual disturbances that include trouble focusing, being more sensitive to lights or sunlight, and have trouble with depth perception. Individuals with neurocognitive deficits also command rehabilitation services to help improve cognition as a result of a decline in mental capacity or function. Such neurocognitive disorders effect various mental aspects including memory, perception, speech and language, and learning. As such individuals elicit the assistance of trained individuals to help rehabilitate a person's vestibular ocular and neurocognitive system.

There are variety of devices and methods available to help diagnose individuals suffering from medical conditions affecting both the vestibular ocular system, and neurocognitive faculties of a person, but few devices and methods are developed to rehabilitate such individuals. One course of treatment involves undergoing vestibular ocular reflex exercises (VOR exercises) in which the goal is to more effectively process communication between the human's inner ears, brain, and eyes. The brain receives signals provided by the inner ears when a person moves their eyes or body, and uses the information to coordinate eye movements so that the person can stabilize their gaze on an object even though their eyes or body are in motion. One technique involves the patient holding a finger of each hand at arm's length directly in front of them, and moving their eyes quickly from one finger to the other, side to side, or up and down, viewing each finger only long enough to establish focus, and then moving their eyes quickly back to the other finger again and viewing that finger only long enough to focus, and repeating the process over again for a certain amount of time. A host of prior art devices and systems have been developed to aid individuals mostly with vestibular ocular issues and lack the ability to also assist such individuals with neurocognitive impairments.

Such conventional devices and methods include a number of drawbacks and aim to diagnose various ocular or neurocognitive conditions rather than rehabilitate individuals suffering from such impairments. Prior art devices and systems developed to assist individual patients with vestibular ocular reflex exercises typically include the use of computers, processors, electrical lights, detectors or sensors, visual display screens, data storage and processing, software applications, and wearable devices. The prior art devices are expensive, sophisticated to program and operate, often require maintenance and repairs that drive up costs associated with rehabilitation services. Also, vestibular ocular reflex exercises that involve patients placing two fingers at a distance in front of them, typically results in patients placing the fingers at random distances, makes it difficult to conform to a controlled setting when patients engage in vestibular ocular reflex exercises, and requires individuals to extend their arms outwards in front of them for prolonged periods of time exhausting the person's capacity to retain the fingers, objectively in place. The random positioning of the fingers, and the subjective nature of the exercise, makes it difficult to objectively determine what improvements are made over time in a clinical setting.

Accordingly, there is an established need for a solution to at least one of the aforementioned problems. There remains a need for a rehabilitation device used for clinical rehabilitation of individuals with vestibular ocular dysfunctions, and neurocognitive impairments, in which the device increases objectivity of patient care, is less sophisticated and complex to use, is adaptable for use with patients of different heights, and allows clinicians to track improvements over time.

SUMMARY OF THE INVENTION

The present invention is directed to a medical rehabilitation device for clinically rehabilitating individuals suffering from medical conditions affecting the vestibular ocular system, and other neurocognitive functions. The rehabilitation device includes a support base having an elongate slot, and a plurality of arms adjustably attached to the support base via, the elongate slot, where each arm includes a magnetic strip for selectively positioning visual targets on the arms to solicit patient recognition of colors and position of the visual targets during both vestibular ocular reflex and other neurocognitive exercises.

A first embodiment provides a rehabilitation device for rehabilitating patients with medical conditions affecting a person's vestibular ocular system, and other neurocognitive functions, where the rehabilitation device comprises: a support base including an elongate rectangular body, a slot formed completely through the body and beginning at a distance from one end of the body and terminating at a distance from another end of the body where the distances define a first stop gap and a second stop gap, a plurality of arms, each arm including an elongate rectangular arm body, and at least one magnetic strip disposed on a top surface and along a longitudinal edge of the arm body, wherein two of the plurality of arms each include a hole formed through a central region of the arm body, and one of the plurality of arms including an end that is perpendicular to the arm body and includes a hole formed within the end, each of the holes and the slot aligned together to receive a fastener there through for releasably attaching any of the plurality of arms to the support base, where two of the plurality of arms independently pivot about the fastener when the two arms are attached to the support base, a plurality of visual targets releasably attachable to any of the magnetic strips, and wherein measurement markings are provided on the top surface of each arm spanning a length of, and disposed adjacent to, each magnetic strip, and the slot of the support base.

In another embodiment, the present invention is directed to a rehabilitation device for a patient with medical conditions affecting a human vestibular ocular system, or other neurocognitive functions, which is mountable to a support surface to facilitate the patient's performance of a plurality of vestibular ocular reflex or other neurocognitive rehabilitation exercises, the rehabilitation device comprising: an elongate support base including a slot formed along a length thereof; at least one arm movably positionable along the length of the elongate support base via a fastener which operatively engages at least a portion of the slot; the at least one arm having a plurality of measurement markings disposed along a length thereof, at least one magnetic strip affixed to a portion of the at least one arm adjacent the plurality of measurement markings; and a plurality of visual targets releasably attachable to the at least one arm via the at least one magnetic strip, wherein each of the plurality of visual targets are attached to the at least one magnetic strip in a different one of a plurality of preselected positions, and each of the plurality of visual targets is retained in a corresponding one of the plurality of preselected positions while the patient performs one of the plurality of rehabilitation exercises.

In one aspect, each of the plurality of arms is constructed from any of a plastic material, including but not limited to, polyvinyl chloride (PVC), polystyrene (PS), high-density polyethylene (HDPE), polycarbonate, synthetic or semi-synthetic polymers, for example: ABS resins, acetyl resins, nylon resins, urethane resins, or high impact polystyrene resins, from nylon, fiberglass, plexiglass, or from a metal material, including but not limited to, stainless steel, aluminum, sheet metal, galvanized steel.

In another aspect, two of the plurality of arms are adjustable in height along the vertical axis of the slot formed within the support base to accommodate use of the rehabilitation device with patients having different heights. The pivoting point defined by the intersection of two arms may be adjusted with the horizontal line of sight to patients when sitting or standing in front of the rehabilitation device.

In another aspect, each of the plurality of visual targets comprise the same or different color and may include any of numbers, symbols, characters, letters, or motif. Each visual target includes a metal or metal particles to provide magnetic attraction to the magnetic strips.

In yet another aspect, the at least one magnetic strip includes a pair of magnetic strips disposed in coaxial alignment on the top surface of at least two arms.

In another aspect, the support base is configured to attach to a vertical surface using any well-known fastener such as nails, screws, bolts and nuts, glue, adhesive, rivets, brackets, clamps, clips, or spring holding detents.

In yet another aspect, one of said plurality of arms includes a depth arm adapted to exercise a patient's perception of depth during vestibular ocular system or other neurocognitive exercises.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a rehabilitation device for clinical rehabilitation of individuals having various medical conditions affecting the person's vestibular ocular system, and other neurocognitive functions, that is used to increase objective measurement of patient progress, and is adaptable for use with patients of different heights.

Figure 1:
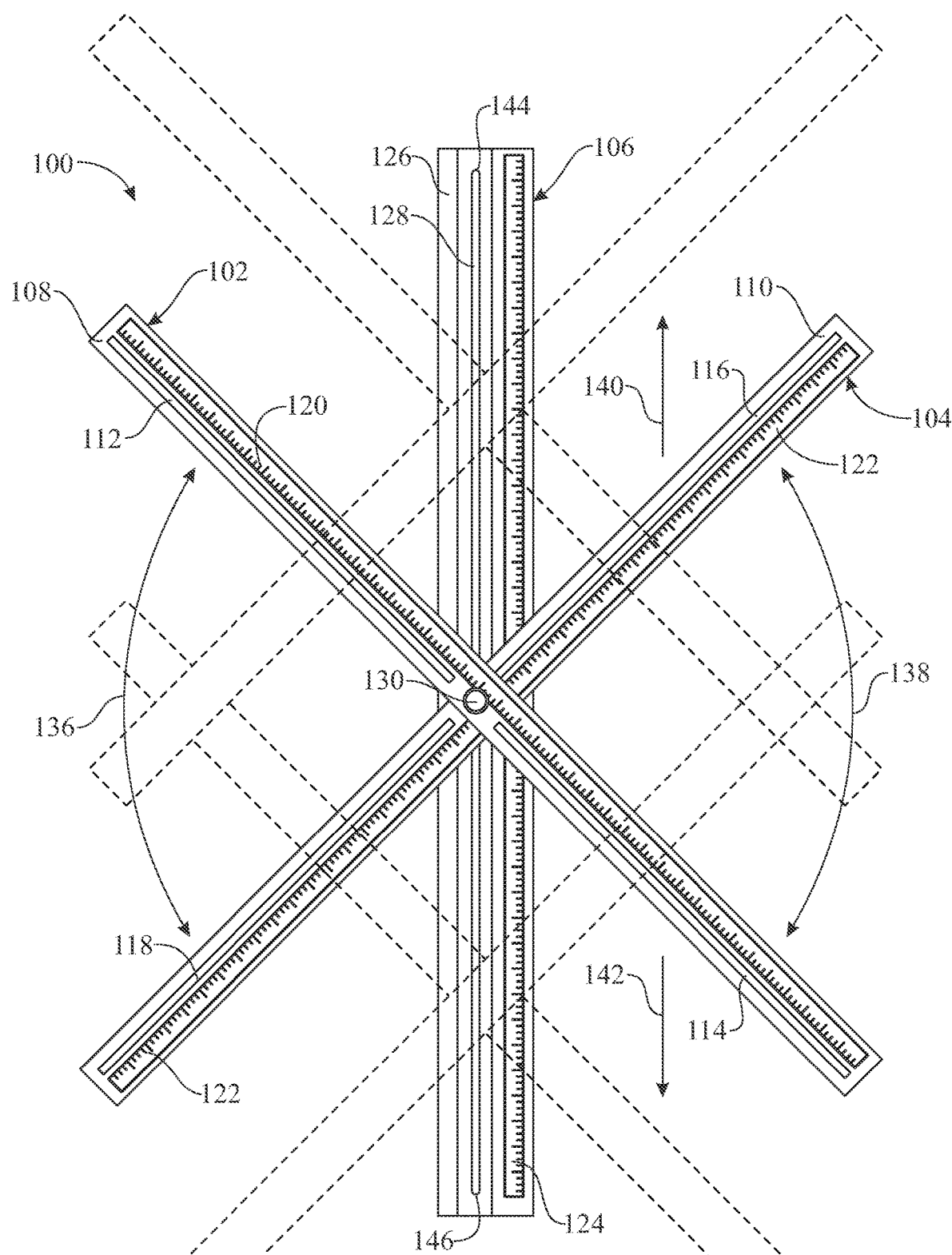
FIG. 1 presents a front view of a rehabilitation device, showing a pair of arms movably attachable at various positions along a vertical axis of a support base having a slot, and readily pivoted with each other about a horizontal, diagonal, and vertical axis, and measurement markings provided on the outer surface of each arm and support base, in accordance with an embodiment of the present invention.
Figure 2:
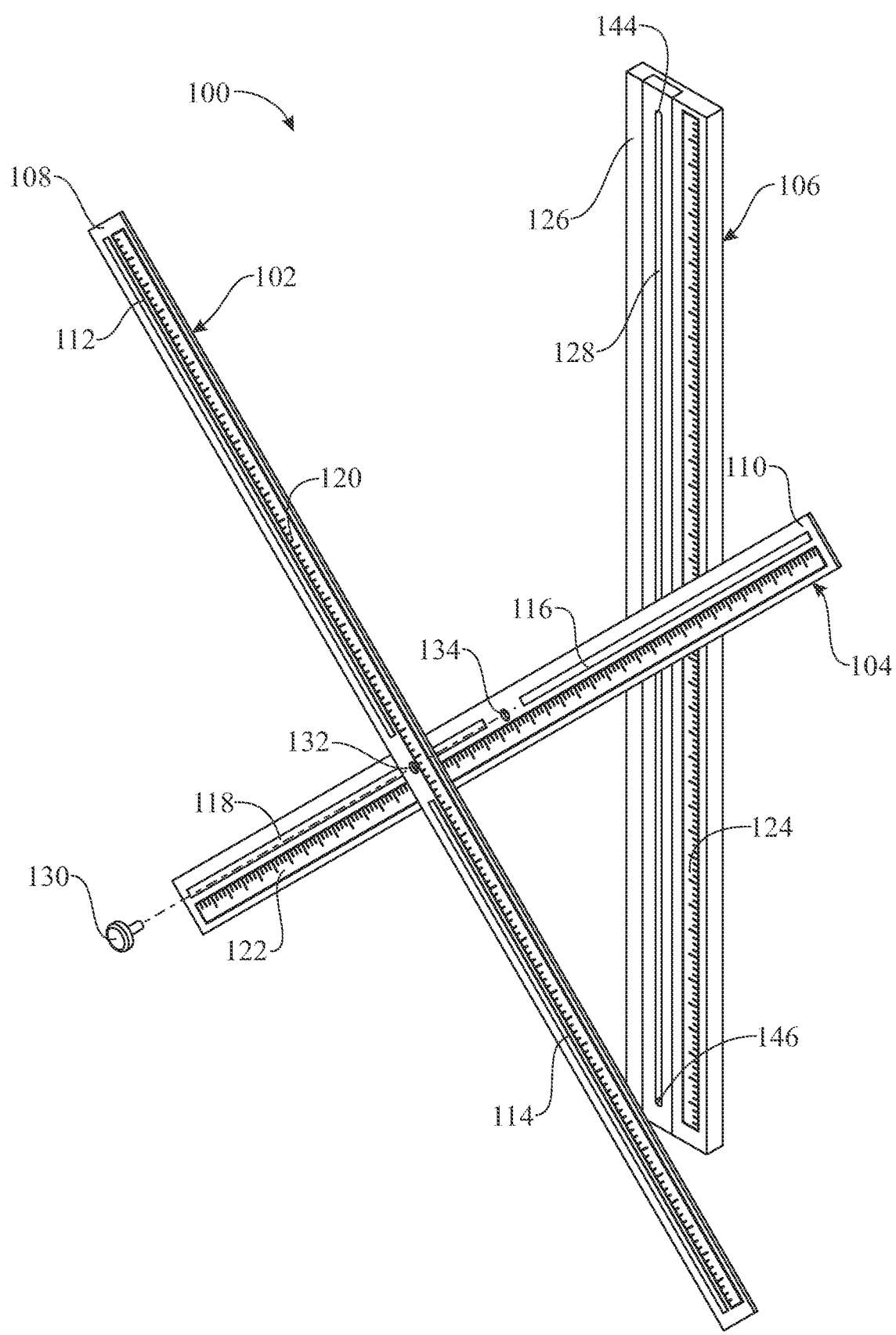
FIG. 2 presents an exploded, perspective view, of the rehabilitation device of FIG. 1, showing the pair of arms detached from the support base, and a fastener adapted to pivotally hold the arms in adjustable positions on the support base, via the slot, in accordance with one embodiment of the present invention.

Referring now to the figures wherein like numerals are represented by like elements throughout, there are shown in FIGS. 1 and 2, a front and an exploded perspective view, respectively, of a rehabilitation device 100 showing a pair of arms 102, 104 movably attachable at various positions along the vertical axis of a support base 106, in which the arms 102, 104 are readily pivoted in vertical, horizontal or diagonal positions, in accordance with an embodiment of the present invention. Each arm 102, 104 comprises a generally, elongate rectangular body 108, 110 having both a predetermined length, width, and thickness. In one embodiment, the arms 102, 104 are symmetrically identical to each other in geometric shape, size, dimension, and construction, however, it will be understood that arms 102, 104 may differ in geometrical shape, size, and dimension to accommodate particular medical testing or procedures. Each arm 102, 104 and the support base 106, is constructed from a rigid, durable material that includes any of plastic, including but not limited to, polyvinyl chloride (PVC), polystyrene (PS), high-density polyethylene (HDPE), polycarbonate, synthetic or semi-synthetic polymers, for example: ABS resins, acetyl resins, nylon resins, urethane resins, or high impact polystyrene resins, from nylon, fiberglass, plexiglass, or from a metal material, including but not limited to, stainless steel, aluminum, sheet metal, galvanized steel. The construction material is selected to provide a durable, lightweight support base 106, and arms 102, 104 making it easier to implement, transport, and handle during use.

Each arm 102, 104 includes a magnetic strip 112, 114, 116, 118 attached to the outer surface of the body 108, 110 by any of a variety of attachments including, but not limited to, glue or other adhesive materials, double face tape, hook and loop fasteners, etc. Each magnetic strip 112, 114, 116, 118 includes a width dimensionally sized to permit magnetic attachment of one or more visual targets 200, 202, 204, 206, as better illustrated in FIG. 3. In one embodiment, each magnet strip 112, 114, 116, 118 extends from opposite ends of each arm 102, 104 and towards each other a predetermined distance terminating in close proximity to a central intersection point of both arms 102, 104 when attached to the support base 106. It will be understood that in one alternative embodiment, each arm 102, 104 may include an elongated slot, rather than magnetic strips, where the slot is formed through the body 108, 110 of the arms 102, 104 for slideable attachment one or more visual targets 200, 202, 204, 206. For example, in one non-limiting embodiment, each visual target 200, 202, 204, 206 may include a head, and a shank attached to, or integrally formed with, the head, where a distal end of the shank is threaded to receive a fastener such as a nut for securing visual targets 200, 202, 204, 206 within each elongate slot.

Figure 3:
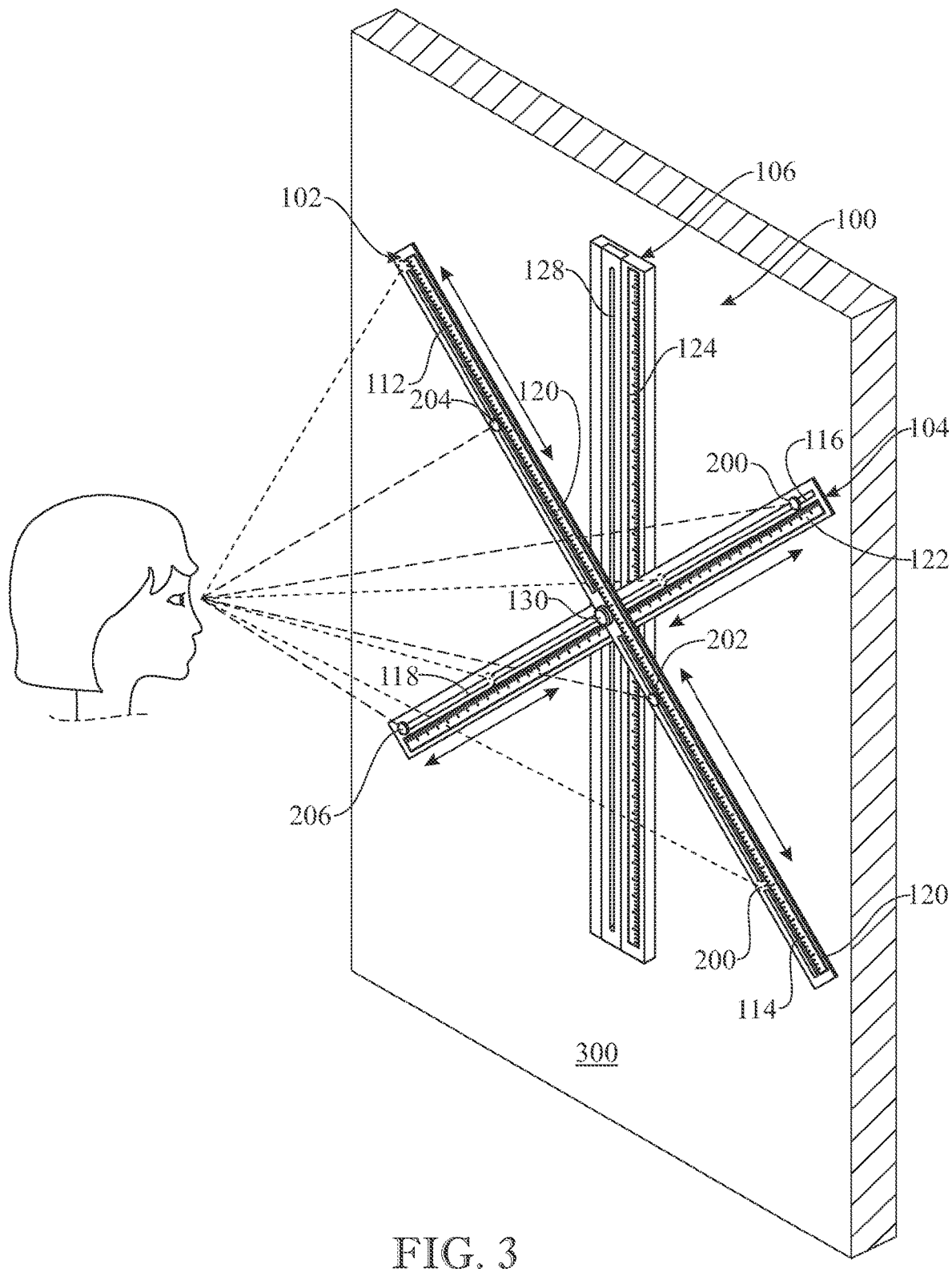
FIG. 3 presents a perspective, operative view, of patient utilizing the rehabilitation device of FIG. 1, showing the support base affixed to a wall, or other support surface, the pair of arms adjustably attached to the support base and vertically positioned in height to accommodate a patient's horizontal line of sight for providing a viewing angle of visual targets disposed on the arms, in accordance with an embodiment of the present invention.

The rehabilitation device 100 includes the use of visual targets 200, 202, 204, 206 that each comprise a body having a round or square or other geometric shape, and includes a metal or steel material, or metallic particles, to permit attachment via magnetic force when attaching the visual targets 200, 202, 204, 206 at selected positions along corresponding ones of the magnetic strips 112, 114, 116, and 118, as generally denoted by direction arrows shown in FIG. 3. For example, each visual target 200, 202, 204, 206 may comprise a plastic housing that encloses, or has embedded therein, a metal or steel member or particles to provide magnetic attraction between the targets 200, 202, 204, 206 and magnetic strips 112, 114, 116, and 118. Each visual target 200, 202, 204, 206 may comprise the same or different color, shape, or size, and include any of letters, numbers, characters, or symbols implemented to vary the difficulty of rehabilitation exercises.

With continued reference to FIGS. 1 and 2, the arms 102, 104, and support base 106 include indicia or markings 120, 122, and 124, respectively, disposed along a longitudinal edge of each body 108, 110, 126 and spanning the length of each arm 102, 104, and support base 106. The markings 120, 122, 124 are disposed adjacent the magnetic strips 112, 114, 116, 118 to provide measured positioning when placing visual targets 200, 202, 204, 206 on the arms 102 and 104. Thus, exact positions of each visual target 200, 202, 204, 206 can be clinically recorded in accordance with measurement markings 120, 122, 124. In one non-limiting embodiment, the markings 120, 122, 124 comprise a system of measurements represented by the U.S. standard or English, Arabic, or Metric measurement system. Thus, in one example, markings 120, 122, 124 may comprise measurements representing millimeters and/or centimeters, or inches and/or fractions of inches. The markings 120, 122, 124 are provided on, or applied to, each arm 102, 104 and the base support 106 using engraving, embossing, stenciling, or other well-known processes. Alternatively, markings 120, 122, 124 may comprise a self-adhesive label, or a magnetic label that is releasably applied to the outer surface of each arm 102, 104 and support base 106. For example, the rehabilitation device 100 may include magnetic labels having different measurements in which the labels are interchangeable allowing clinicians to switch between different measurement systems as desired.

The support base 106 comprises an elongate rectangular shaped body 126 having a predetermined length, width, and thickness, and includes an elongate slot 128 beginning a distance from one end of the support base 106 and terminating a distance from another end of the support base 106, defined by stop gaps 144 and 146. The size and shape of the elongate slot 128 is configured to accommodate removable insertion of a fastener 130 there through which is employed to moveably attach the arms 102, 104 along a vertical axis of the support base 106. As shown in FIG. 2, each arm includes a hole 132, 134 configured to receive the shank of a fastener 130 there through to movably retain the arms 102, 104 to the support base 106. In a preferred embodiment, each hole 132, 134 is formed through the central region of the body 108, 110, of each arm 102, 104, respectively, such that the distance from one end of each arm 102, 104 to respective holes 132, 134, and the distance from another end of each arm 102, 104 to the respective holes 132, 134, is generally the same. As illustrated in FIG. 2, the holes 132, 134 of each arm 102, 104 align with each other and with the opening of the elongate slot 128 of the support base 106 to permit insertion of the fastener 130 for securely holding the arms 102, 104 to the base 106. It will be appreciated that the length of the shank of the fastener 130 is selected to pass through the holes 132, 134 and the elongate slot 128 of the support base 106 to adjustably secure the arms 102, 104 to the base 106. The fastener 130 may comprise a variety of different fasteners, fastening systems or devices. For example, the fastener 130 may comprise a bolt and nut, bolt and wing-nut, spring detent mechanism, push-pull lock, and, in at least one embodiment, the fastener 130 may include washers, lock-washers, or spacers. In one embodiment, the fastener 130 includes a wing-nut to provide ease of access for users when adjusting rotational and vertical positioning of the arms 102 and 104.

With continued reference to FIG. 1, each arm 102, 104 is adjustable in a vertical, horizontal, or diagonal position, and movable along a vertical axis of the support base 106, as denoted by directional rotation arrows 136, 138, a vertical upward positioning arrow 140, and a downward positioning arrow 142. Rotational arrows 136, 138 illustrate rotational movement of the arms 102, 104 about a central point of intersection defined by fastener 130. Adjustment of the arms 102, 104 along a vertical axis on the support base 106, is depicted by phantom lines showing the arms 102, 104 positioned towards a top and bottom region of the support base 106. The stop gaps 144, 146 are employed to prevent the fastener 130 and arms 102, 104 from sliding completely through the elongate slot 128 of the support base 106 during adjustment and use.

Turning now to FIG. 3, there is shown a perspective, operative view and method of use of the rehabilitation device 100 used to rehabilitate a patient suffering from medical conditions affecting the vestibular ocular system, and other neurological functions, in accordance with the present invention. In use, the support base 106 is permanently, or removably affixed to a wall, of other support surface, generally denoted at 300, using, by way of example only, one or more fasteners, nails, rivets, hook and loop fasteners, brackets, supports, releasable connectors, or adhesive. Each arm 102, 104 is adjustably attached to the support base 106 via fastener 130 that is inserted through holes 132, 134 and the elongate slot 128 of the base 106 and secured in place with a nut or similar structure. The attached arms 102, 104 are vertically adjustable along a vertical axis of the support base 106 to accommodate a patient's height to provide a horizontal line of sight that encompasses the viewing angle of visual targets 200, 202, 204, 206 selectively positioned on the magnetic strips 112, 114, 116, 118 on each arm 102 and 104. The patient may be sitting or standing at a predetermined distance in front of the rehabilitation device 100. The arms 102, 104 are adjustable along a vertical axis between a predetermined maximum and minimum height defined by both the length of the support base 106, and the length of the elongate slot 128. In at least one embodiment, markings 124 are provided on the support base 106 to correlate to a height of the patient. For example, if a patient's horizontal line of sight is determined to be 5 feet, 3 inches, then the central point of intersection of both arms 102, 104 can be adjusted in accordance with prescribed markings of 5 feet, 3 inches provided on the markings 124 of the support base 106. In clinical settings, the visual targets 200, 202, 204, 206 span the perimeter of the arms 102, 104 at different distances from the central point of intersection of the arms 102, 104, allowing for variable difficulty in vestibular ocular reflex exercises. The arms 102, 104 are adjustable to form different angles relative to one another to tax the vestibular ocular system in planes of vision.

One or more visual targets 200, 202, 204, 206 are placed randomly at various positions on a corresponding one of the plurality of magnetic strips 112, 114, 116, 118 positioned on arms 102, 104 to provide objective testing when patients, engage in vestibular ocular reflex exercises. As such, each visual target 200, 202, 204, 206 is magnetically retained in selected positions on one of arms 102, 104 as opposed to a patient placing and attempting to retain two fingers in front of them at a distance, wherein the fingers constantly move or droop from position thus taxing objectivity of the exercise. One method of use, requires patients to move their eyes quickly from one visual target 200, 202, 204, 206 to another, side to side, or up and down within the viewing angle, viewing each target 200, 202, 204, 206 only long enough to establish focus, and then moving their eyes quickly back to another visual target 200, 202, 204, 206 and viewing that other target 200, 202, 204, 206 only long enough to focus, and repeating the process over again for a certain amount of time, and with selected targets 200, 202, 204, 206 without the visual targets 200, 202, 204, 206 shifting or moving during the exercise. Adjusting the horizontal, vertical, or diagonal position of the arms 102, 104 correspondingly changes the positioning of the visual targets 200, 202, 204, 206 as well, thus allowing clinicians to adjust the difficulty in vestibular ocular exercises forcing the patients to change their patterns of movement during exercise. As such, clinicians are able to make charted improvements knowing that the visual targets 200, 202, 204, 206 remain in fixed positions at all times during vestibular ocular reflex exercise sessions. Clinicians can chart visual target progression in recognizing color, type and/or position of visual targets 200, 202, 204, 206 from week to week.

The rehabilitation device 100 is also used in neurocognitive aspects of rehabilitation that elicits improvements in cognition. Neurocognitive rehabilitation is important for baseline, immediate asymptomatic exercise in a symptomatic population. In one aspect, restoration rehabilitation allows patients to examine the device 100 and recognize or notice colored targets 200, 202, 204, 206. A patient begins a rehabilitation exercise when a practitioner or technician calls out a color, which then causes patients to elicit a neurocognitive response and recall where the color was located. In at least one embodiment, this rehabilitation exercise is repeated until the patient is comfortable with recalling colors and/or positions of the visual targets 200, 202, 204, and 206. This can also take place where the visual targets 200, 202, 204, 206 comprise any of numbers, symbols, letters, or other form of indicia. Thus, having patients recall numbers, or letters, or numbers instead of, or in addition to, colors and positions of visual targets.

Another neurocognitive rehabilitation exercise includes substitution rehabilitation in which patients initially view the position of visual targets 200, 202, 204, 206 that are placed in selective positions on the arms 102, 104, and then removing the visual targets 200, 202, 204, 206 and having the patients recall from memory the original location of the visual targets 200, 202, 204, 206 while the targets 200, 202, 204, 206 have been removed. For example, black magnets or other color blocking covers can be placed over the visual targets 200, 202, 204, 206 and then reveal the color to the patients to determine if the patients correctly remembered the original location of the visual targets 200, 202, 204, 206 with that color. As such, clinicians can interchange visual targets 200, 202, 204, 206 and instruct patients to look for or find a visual target having a certain color or indicia. The ability to recall prior location or position of visual targets 200, 202, 204, 206 on the arms 102, 104, in addition to concentrating on vestibular ocular reflex exercises provides a unique form of rehabilitation.

Figure 4:
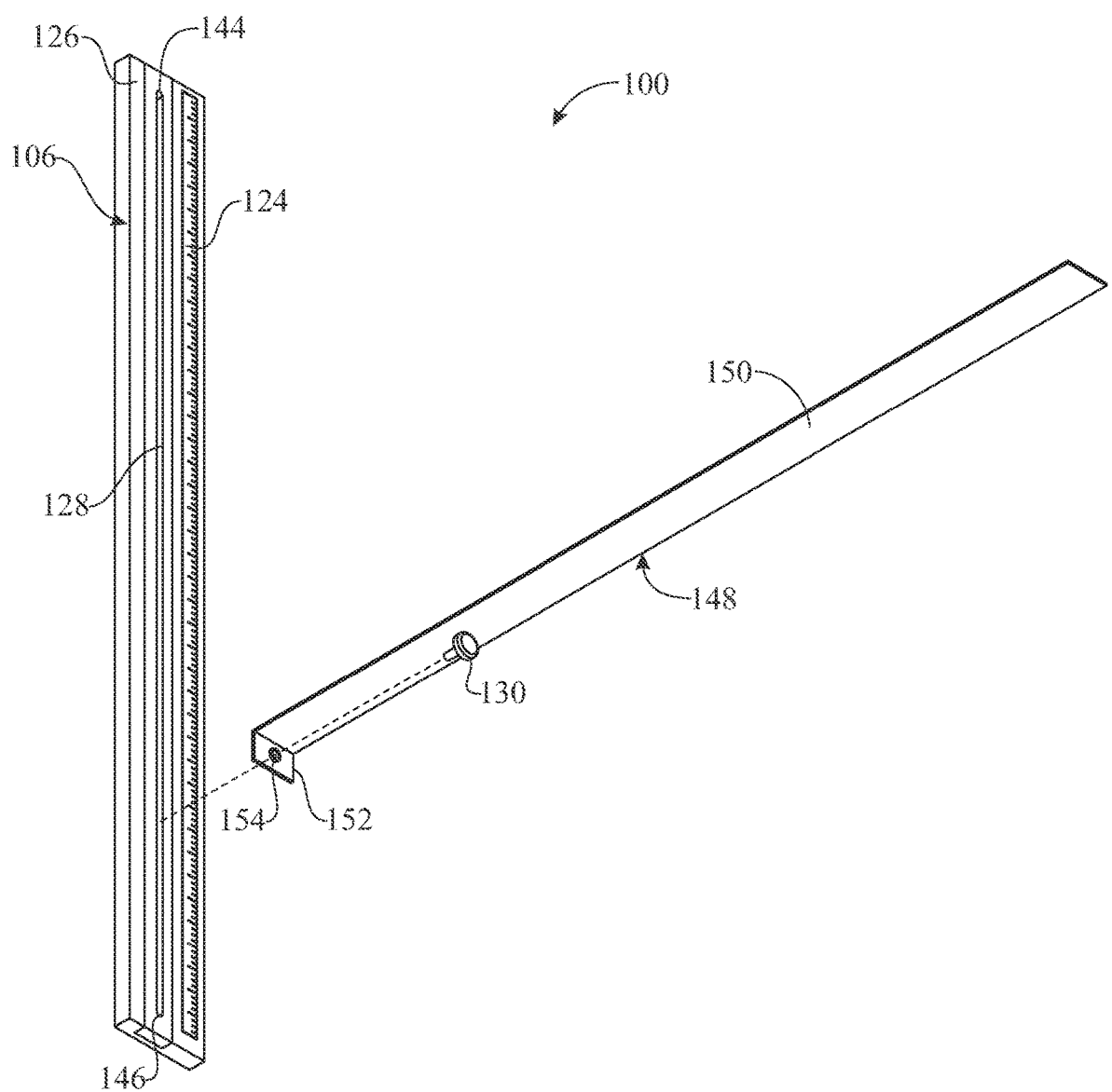
FIG. 4 presents a perspective, exploded view, of the rehabilitation device, showing a bottom view of a depth arm movably attachable at various positions along the vertical axis of the support base via a fastener, in accordance with another embodiment of the present invention.
Figure 5:
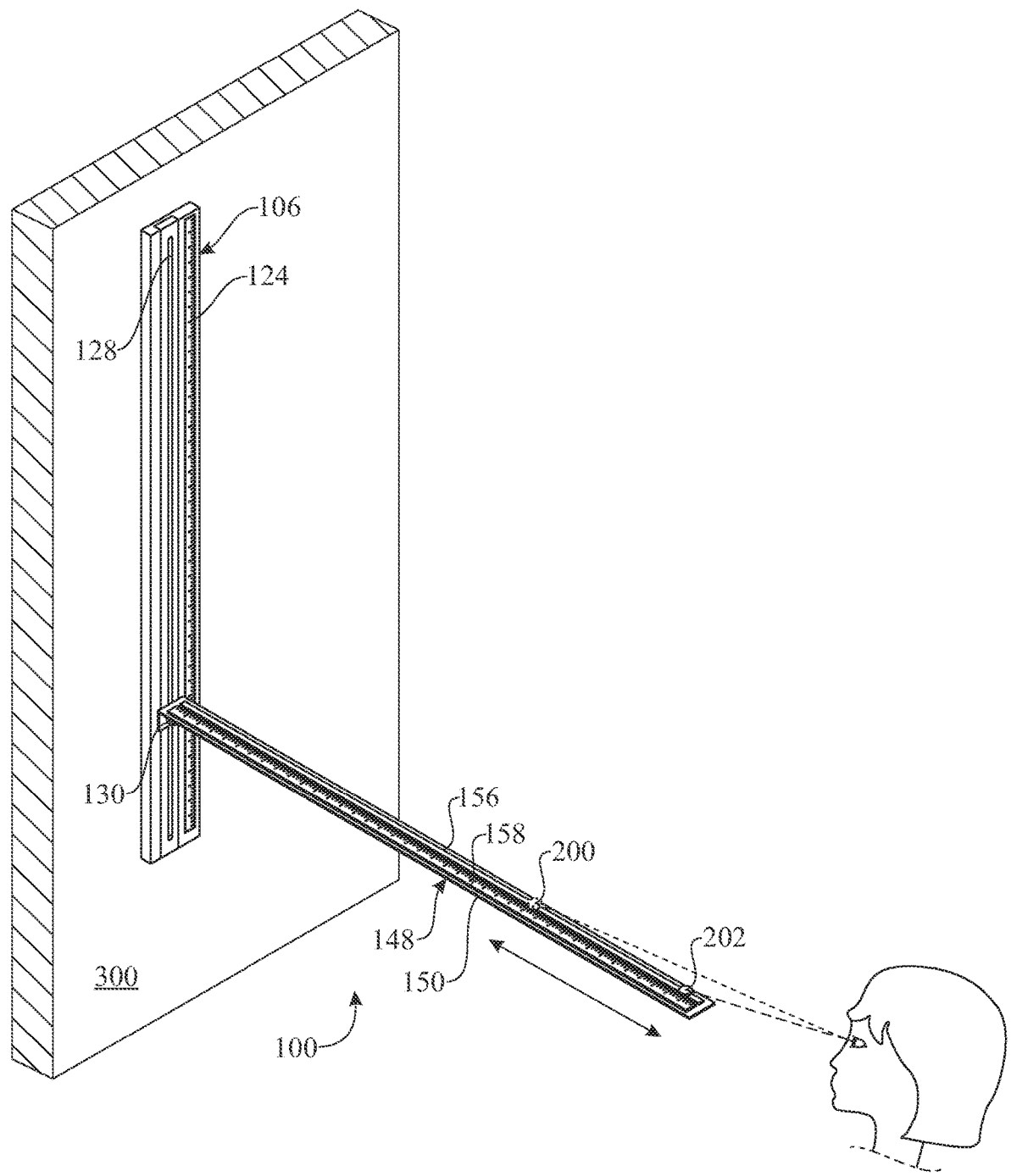
FIG. 5 presents a perspective, operative view, of a patient utilizing the rehabilitation device of FIG. 4, showing the support base affixed to a wall, or other support surface, and the depth arm adjustably attached along the vertical axis of the support base, where the depth arm includes markers situated within the horizontal line of sight of the patient, in accordance with an embodiment of the present invention.

Turning to FIGS. 4 and 5, the rehabilitation device 100 also employs a depth arm to exercise a patient's perception of depth during rehabilitation and provide near point convergence training. In this setup, the pair of arms 102, 104 are replaced with a depth arm 148 comprising a generally, elongate rectangular body 150 having one end that is bent to form a support end 152 that is perpendicular to the longitudinal axis of the body 150. A hole 154 is provided in the support end 152 to adjustably attach the depth arm 148 at various vertical positions within the slot 128 of the support base 106 via, the fastener 130. As with arms 102, 104, depth arm 148 includes a magnetic strip 156 that is attached to the upper surface of the body 150, once again, via glue, adhesive material, double face tape, hook and loop fasteners, etc. The magnetic strip 156 is configured to magnetically attach one or more visual targets 200, 202, 204, 206 in various positions along the depth arm 148.

The depth arm 148 includes indicia or markings 158 similar in nature to the markings 120, 122 provided on arms 102, 104, respectively, disposed along a longitudinal edge of the body 150 and spanning the length of the arm 148. The markings 158 are disposed adjacent the magnetic strip 156 to provide measured positioning of visual targets 200, 202, 204, 206 on the arm 148. Thus, the exact position of each visual target 200, 202, 204, 206 can be recorded based on the positional markings 158 to provide an objective method for exercising and properly charting improvements of patients near point convergence training.

With reference to FIGS. 4 and 5, in use the support base 106 is permanently or removably affixed to a wall, or other support surface, generally denoted at 300, using, once again, one or more fasteners, nails, rivets, hook and loop fasteners, brackets, supports, releasable connectors, double face tape, or adhesive, etc. The depth arm 148 is adjustably attached to the support base 106 via fastener 130 inserted through hole 154 and the elongate slot 128 of the base 106, and secured in place with a nut or similar structure retained on the back of the support base 106. The depth arm 148 is positioned along a vertical axis of the support base 106 to accommodate a patient's height and horizontal line of sight to encompass a viewing angle for seeing visual targets 200, 202 selectively positioned along the magnetic strip 156 of the depth arm 148, such as is shown in FIG. 5. The depth arm 148 is adjustable along a vertical axis between a predetermined maximum and minimum height defined by both the length of the support base 106, and the length of the elongate slot 128. As before, the markings 124 provided on the support base 106 may correlate to a height of a patient. In a clinical setting, one or more of the visual targets 200, 202, 204, 206 are placed randomly at various positions on the magnetic strip 156 spanning the perimeter of the arm 148 at different distances from the distal end of the arm 148, as denoted by the horizontal direction arrow, to allow variable difficulty in either vestibular ocular reflex, or neurocognitive exercises. A patient stands a predetermined distance from the distal end of the depth bar 148, and clinicians elicit the patient's recognition or identification regarding the type, color, and/or position of visual targets 200, 202, 204, 206 in providing near point convergence exercises.

The rehabilitation device 100 is adaptable for rehabilitating patients with vestibular ocular dysfunctions, and includes a pair of arms 102, 104 that are adjustable along a vertical axis of a support base 106 to accommodate patients of different heights, whether sitting or standing, where the arms are adjustable horizontally, diagonally, and vertically to tax the vestibular ocular system in planes of vision. Visual targets 200, 202, 204, 206 are releasably attached to various positions on the arms 102, 104 to provide a temporarily fixed point for use during vestibular ocular reflex exercises where clinicians elicit patient recognition or identification of the type, color, and/or position of visual targets 200, 202, 204, 206 to provide an objective test and allow charted improvements in a clinical setting. The rehabilitation device 100 is also used to rehabilitate patients having neurocognitive impairments as a result of injury, trauma, or disease where patients participate in restoration and substitution rehabilitation exercises to recognize type, color and positioning of visual targets 200, 202, 204, 206 that are strategically placed at various positions on magnetic strips 112, 114, 116, 118 of each arm 102 and 104. The device 100 also is tailored to rehabilitate patients by providing near point convergence exercises by employing a depth arm 148 adjustably attached to the support base 106, via slot 128, and positioning one or more of visual targets 200, 202, 204, 206 at selected measured positions via, markings 158 on the magnetic strip 156 of the arm 148 for patients to identify and recall the type, color and/or position of the targets during exercises.

Other modifications to the rehabilitation device 100 may be made such as adding a magnetic strip to the support base 106 to allow positioning of visual targets 200, 202, 204, 206 on the support base 106 as well if desired. A carrying case, pouch, or storage container may be provided to hold and store disassembled parts such as the arms 102, 104, 148, and support base 106 for easy transport.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A rehabilitation device for a patient with medical conditions affecting a human vestibular ocular system, or other neurocognitive functions, which is mountable to a support surface to facilitate the patient's performance of a plurality of vestibular ocular reflex or other neurocognitive rehabilitation exercises, said rehabilitation device comprising:
- an elongate support base including a slot formed along a length thereof;
- at least one arm movably positionable along said length of said elongate support base via a fastener which operatively engages at least a portion of said at least one arm and said slot;
- said at least one arm having a plurality of measurement markings disposed along a length thereof,
- at least one magnetic strip affixed to a portion of said at least one arm adjacent said plurality of measurement markings; and
- a plurality of visual targets releasably attachable to said at least one arm via said at least one magnetic strip, wherein each of said plurality of visual targets is attached to said at least one magnetic strip in a different one of a plurality of preselected positions, and each of said plurality of visual targets is retained in a corresponding one of said plurality of preselected positions while the patient performs one of the plurality of rehabilitation exercises.

2. The rehabilitation device as recited in claim 1 wherein said slot extends along said length of said elongate support base beginning at a distance from one end of said elongate support base and ending at a distance from an opposite end of said elongate support base.

3. The rehabilitation device as recited in claim 2 wherein said distance from said one end of said elongate support base at least partially defines a first stop gap and said distance from said opposite end of said elongate support base at least partially defines a second stop gap.

4. The rehabilitation device as recited in claim 3 wherein said first stop gap and said second stop gap prevent said fastener from sliding out of said slot.

5. The rehabilitation device as recited in claim 1 wherein said support base is mounted to the support surface such that said slot is disposed in a vertical orientation.

6. The rehabilitation device as recited in claim 5 wherein said at least one arm is movably positionable along said length of said elongate support base via said slot to accommodate the height of the patient.

7. The rehabilitation device as recited in claim 1 wherein said at least one arm is movably positionable along said length of said elongate support base via said slot to accommodate the height of the patient.

8. The rehabilitation device as recited in claim 7 wherein said at least one arm is movably positioned along said length of said elongate support base via said slot to provide a horizontal line of sight based upon the height of the patient.

9. The rehabilitation device as recited in claim 8 wherein said at least one arm is movably positioned along said length of said elongate support base via said slot wherein said horizontal line of sight encompasses a viewing angle which allows the patient to see said plurality of visual targets attached to said at least one arm.

10. The rehabilitation device as recited in claim 1 wherein said at least one arm comprises a depth arm, wherein said depth arm extends outwardly from said elongated support base towards the patient.

11. The rehabilitation device as recited in claim 1 further comprising a plurality of arms.

12. The rehabilitation device as recited in claim 11 wherein said at least one of said plurality of arms comprises a depth arm, wherein said depth arm extends outwardly from said elongated support base towards the patient.

13. The rehabilitation device as recited in claim 1 wherein each of said plurality of visual targets comprises one or more of a plurality of different colors.

14. The rehabilitation device as recited in claim 1 wherein each of said plurality of visual targets comprises one or more of a different number, symbol, character, letter or motif visible thereon.

15. A rehabilitation device for a patient with medical conditions affecting a human vestibular ocular system, or other neurocognitive functions, which is mountable to a support surface to facilitate the patient's performance of a plurality of vestibular ocular reflex or other neurocognitive rehabilitation exercises, said rehabilitation device comprising:
- an elongate support base including a slot formed along a length thereof;
- a plurality of arms movably positionable along said length of said elongate support base via a fastener which operatively engages at least a portion of said slot;
- each of said plurality of arms having a plurality of measurement markings disposed along a corresponding length thereof,
- at least one magnetic strip affixed to a portion of each of said plurality of arms adjacent said plurality of measurement markings; and
- a plurality of visual targets releasably attachable to each of said plurality of arms via a corresponding one of said magnetic strips, wherein each of said plurality of visual targets is attached to said corresponding one of said magnetic strips in a different one of a plurality of preselected positions, and each of said plurality of visual targets is retained in a corresponding one of said plurality of preselected positions while the patient performs one of the plurality of rehabilitation exercises.

16. The rehabilitation device as recited in claim 15 wherein each of said plurality of arms is movably positionable along said length of said elongate support base via said slot to accommodate the height of the patient.

17. The rehabilitation device as recited in claim 16 wherein each of said plurality of arms is movably positioned along said length of said elongate support base via said slot to provide a horizontal line of sight based upon the height of the patient.

18. The rehabilitation device as recited in claim 17 wherein each of said plurality of arms is movably positioned along said length of said elongate support base via said slot wherein said horizontal line of sight encompasses a viewing angle which allows the patient to see said plurality of visual targets attached to said at least one arm.

19. The rehabilitation device as recited in claim 15 further comprising a pivot point at least partially defined at an intersection of two of said plurality of arms, wherein said pivot point is adjustably positioned along said length of said elongate support base via said slot to provide a horizontal line of sight to the patient sitting or standing in front of said rehabilitation device.

20. A rehabilitation device for a patient with medical conditions affecting a human vestibular ocular system, or other neurocognitive functions, which is mountable to a support surface to facilitate the patient's performance of a plurality of vestibular ocular reflex or other neurocognitive rehabilitation exercises, said rehabilitation device comprising:

a support base having an elongate rectangular body including a slot formed along and through at least a portion of a length of said elongate rectangular body;

a plurality of arms movably positionable along said length of said elongate support base via a fastener which operatively engages at least a portion of each of said plurality of arms and said slot, each of said plurality of arms is movably positioned along said length of said elongate support body via said slot to provide a horizontal line of sight based upon the height of the patient;

each of said plurality of arms comprising an elongated arm body, a plurality of measurement markings disposed along a corresponding length of said elongated arm body of each of said plurality of arms;

a plurality of magnetic strips affixed to separate portions of said elongated arm body of each of said plurality of arms adjacent said plurality of measurement markings;

a plurality of visual targets releasably attachable to each of said plurality of arms via a corresponding one of said magnetic strips, at least a portion of each of said plurality of visual targets comprises a magnetically attractive material of construction; and each of said plurality of visual targets are attached to said corresponding one of said magnetic strips in a different one of a plurality of preselected positions, and each of said plurality of visual targets is retained in a corresponding one of said plurality of preselected positions while the patient performs one of the plurality of rehabilitation exercises.

\* \* \* \* \*